(12) United States Patent
Yuba

(10) Patent No.: US 11,471,310 B2
(45) Date of Patent: Oct. 18, 2022

(54) INDWELLING DEVICE AND CYLINDRICAL TREATMENT TOOL

(71) Applicant: SB-KAWASUMI LABORATORIES, INC., Kanagawa (JP)

(72) Inventor: Toshiyasu Yuba, Tokyo (JP)

(73) Assignee: SB-KAWASUMI LABORATORIES, INC., Kanagawa (JP)

( * ) Notice: Subject to any disclaimer, the term of this patent is extended or adjusted under 35 U.S.C. 154(b) by 0 days.

(21) Appl. No.: 16/971,696

(22) PCT Filed: Mar. 18, 2019

(86) PCT No.: PCT/JP2019/011058
§ 371 (c)(1),
(2) Date: Aug. 21, 2020

(87) PCT Pub. No.: WO2019/181821
PCT Pub. Date: Sep. 26, 2019

(65) Prior Publication Data
US 2020/0405520 A1  Dec. 31, 2020

(30) Foreign Application Priority Data

Mar. 19, 2018 (JP) .............................. JP2018-051632

(51) Int. Cl.
A61F 2/962 (2013.01)
A61F 2/90 (2013.01)
A61F 2/966 (2013.01)

(52) U.S. Cl.
CPC ................ *A61F 2/962* (2013.01); *A61F 2/90* (2013.01); *A61F 2/9662* (2020.05)

(58) Field of Classification Search
CPC .......... A61F 2/962; A61F 2/9662; A61F 2/90; A61F 2002/9665; A61F 2/07;
(Continued)

(56) References Cited

U.S. PATENT DOCUMENTS

2004/0220585 A1* 11/2004 Nikolchev ....... A61B 17/12136
606/108
2007/0250151 A1* 10/2007 Pereira ..................... A61F 2/95
623/1.12

(Continued)

FOREIGN PATENT DOCUMENTS

JP       2001-526574       12/2001
JP       2008-119481       5/2008
(Continued)

OTHER PUBLICATIONS

International Search Report and the Written Opinion dated Jun. 11, 2019 From the International Searching Authority Re. Application No. PCT/JP2019/011058 and its Translation of Search Report Into English. (11 Pages).

*Primary Examiner* — Tuan V Nguyen
*Assistant Examiner* — Bridget E. Rabaglia

(57) ABSTRACT

An indwelling device 1 is provided with: a sheath 20 that is capable of housing a stent graft 10; and a long shaft 30 that is configured to be capable of advancing or retreating inside the sheath along the axial direction. The shaft has a fixing tool 34 and a hollow tube 35 that are respectively engaged with a connection part 14 and a blood vessel wall fixing part 15 of the stent graft to restrict movement of an opening end 11a of the stent graft in the radial direction. The indwelling device is configured to be capable of releasing engagement between the connection part and the fixing tool and engagement between the blood vessel wall fixing part and the hollow tube independently of each other by displacing the shaft with respect to the stent graft in the axial direction.

8 Claims, 4 Drawing Sheets

(58) Field of Classification Search
CPC .... A61F 2/848; A61F 2/86; A61F 2/95; A61F 2/966; A61F 2/9661; A61F 2002/8486; A61F 2002/9505; A61F 2002/072; A61F 2002/075; A61F 2002/077; A61F 2002/9623; A61F 2/97; A61F 2002/9528; A61F 2002/9534
USPC .................................................. 623/1.11, 1.23
See application file for complete search history.

(56) References Cited

U.S. PATENT DOCUMENTS

| | | | |
|---|---|---|---|
| 2008/0039927 A1 | 2/2008 | Barr | |
| 2008/0114442 A1 | 5/2008 | Mitchell et al. | |
| 2008/0262590 A1 * | 10/2008 | Murray | A61F 2/95 623/1.11 |
| 2014/0236278 A1 | 8/2014 | Argentine et al. | |
| 2017/0079819 A1 | 3/2017 | Pung et al. | |

FOREIGN PATENT DOCUMENTS

| | | | |
|---|---|---|---|
| JP | 2009-534157 | 9/2009 | |
| JP | 4928449 | 5/2012 | |
| JP | 5408866 | 2/2014 | |
| JP | 6261619 | 1/2018 | |
| WO | WO 98/53761 | 12/1998 | |
| WO | WO 2017/049312 | 3/2017 | |
| WO | WO-2017195125 A1 * | 11/2017 | A61F 2/0095 |
| WO | WO 2019/181821 | 9/2019 | |

* cited by examiner

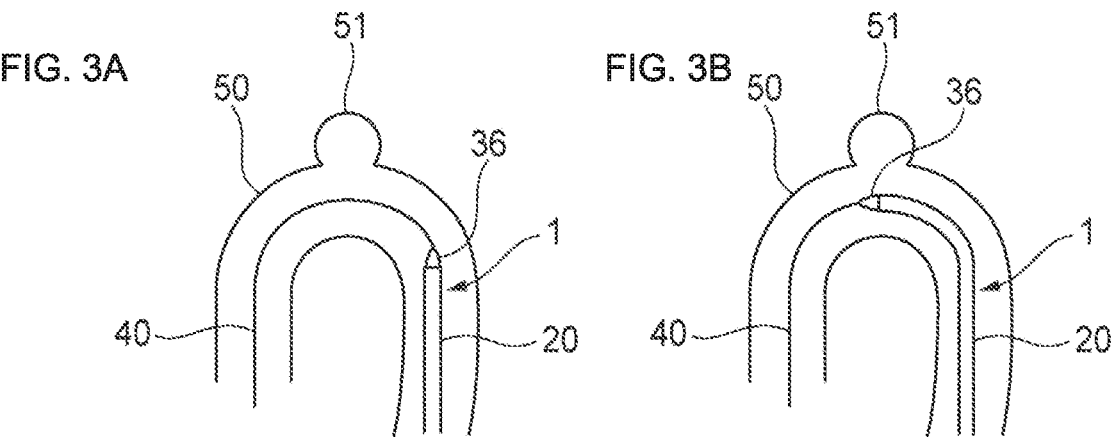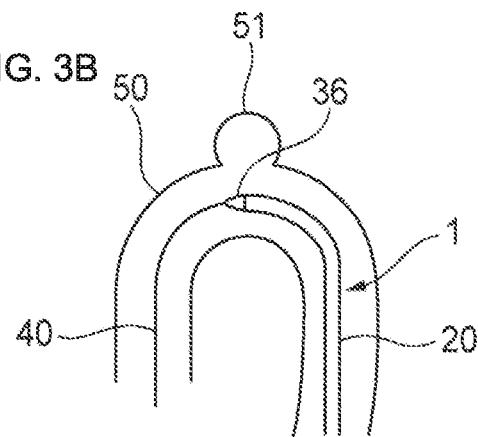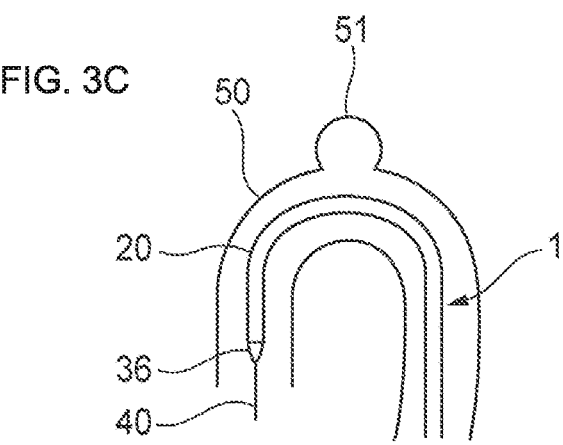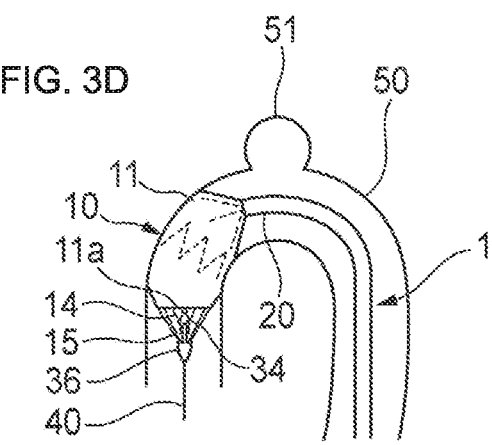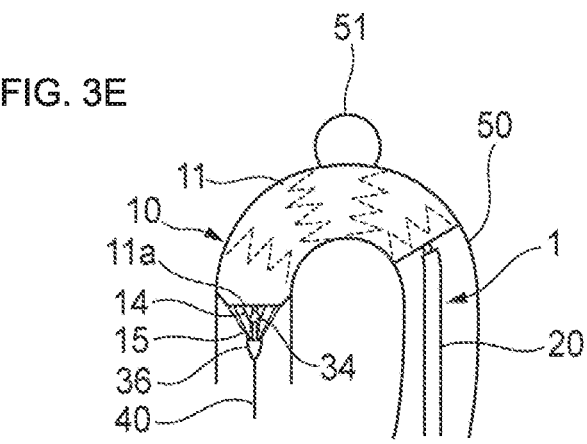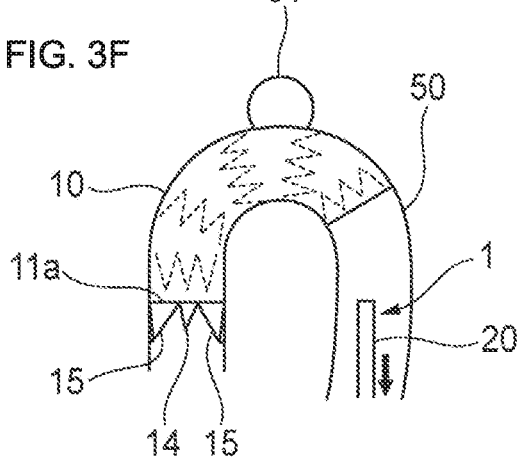

INDWELLING DEVICE AND CYLINDRICAL TREATMENT TOOL

TECHNICAL FIELD

The present invention relates to an indwelling device and a cylindrical treatment tool.

BACKGROUND ART

Conventionally, there are several known cylindrical treatment tools such as a stent graft used for treatment of aneurysm or the like generated in a blood vessel wall, and indwelling devices for delivering and indwelling a cylindrical treatment tool to an affected part (see Patent Documents 1-3). Generally, these types of indwelling devices are made to indwell a cylindrical treatment tool on an affected area by delivering the cylindrical treatment tool in a radially contracted state to the affected area and expanding radially the cylindrical treatment tool in the affected area.

For example, one of the conventional indwelling devices is made to be capable of indwelling a so-called later-opening-head cylindrical treatment tool. Specifically, this indwelling device has a head chip capable of housing an arm part disposed on an open end of the main part of the cylindrical treatment tool, so as to deliver the cylindrical treatment tool to an affected area, with the arm part left housed in the head chip, and to expand the main part at the affected area, followed by releasing the arm part from the head chip to allow it to come into contact with a blood vessel wall (see Patent Document 1).

PRIOR ART DOCUMENT

Patent Document

Patent Document 1: Japanese Patent No. 5408866
Patent Document 2: Japanese Patent No. 4928449
Patent Document 3: Japanese Patent No. 6261619

SUMMARY OF THE INVENTION

Technical Problem

The conventional indwelling device mentioned above has two shafts as a mechanism that releases the arm part housed in the head chip: a shaft connected to the head chip that houses the arm part, and a shaft that holds the arm part relatively movable relative to the head chip. Since these two shafts have a dual structure in which one shaft is inserted into the hollow part of the other shaft, a sheath that houses the cylindrical treatment tool is likely to have an increased diameter. However, in view of reducing invasiveness on a patient's body or the like, it is desirable that the sheath have a reduced diameter.

The present invention has been made in view of the above-described circumstances, and an object thereof is to provide a reduced diameter of a sheath that houses a cylindrical treatment tool, thus achieving to reduce invasiveness on the patient's body.

Solution to Problem

The indwelling device according to the present invention is
an indwelling device that causes a cylindrical treatment tool, which is radially expandable, to indwell a living body lumen, the indwelling device comprising:
a sheath in a tubular shape that is capable of housing the cylindrical treatment tool, and
a shaft member in an elongated shape configured to move back and forth inside the sheath along an axial direction of the sheath,
wherein the shaft member
has a first controlling part and a second controlling part that engage with a first engaging part and a second engaging part of the cylindrical treatment tool, respectively, to control radial movement of an opening end of the cylindrical treatment tool,
and wherein the shaft member is displaced relative to the cylindrical treatment tool in the axial direction to allow a first engagement between the first controlling part and the first engaging part and a second engagement between the second controlling part and the second engaging part to be released independently of each other.

Furthermore, the cylindrical treatment tool according to the present invention is
a cylindrical treatment tool that is caused to indwell a living body lumen using an indwelling device, the cylindrical treatment tool comprising:
a main part in a tubular shape configured to radially expand, and
a first engaging part and a second engaging part each protruding in a direction away from one opening end of the main part in an axial direction of the main part by a predetermined protrusion length and configured to engage with the indwelling device;
wherein the first engaging part and the second engaging part
each engage with the indwelling device to allow control of radial movement of the one opening end, and each independently make engagement with the indwelling device releasable.

Advantageous Effect of the Invention

According to the present invention, it is possible to provide a reduced diameter of a sheath that houses the cylindrical treatment tool, and to achieve to reduce invasiveness on a patient's body.

So far, the present invention has been briefly described. Furthermore, the details of the present invention will be further clarified by reading through the embodiments for performing the invention described below (hereinafter referred to as "embodiment") with reference to the accompanying drawings.

BRIEF DESCRIPTION OF THE DRAWINGS

FIGS. 3A to 3F are a series of views for illustrating a procedure for indwelling the cylindrical treatment tool into a blood vessel using the indwelling device.

FIG. 4A corresponds to FIGS. 3A to 3C, FIG. 4B corresponds to FIGS. 3D to 3E, and FIGS. 4C to 4D correspond to FIG. 3F.

DESCRIPTION OF THE EMBODIMENT

[Cylindrical Treatment Tool and Indwelling Device]

In the present embodiment, a stent graft 10 is used as a cylindrical treatment tool to be indwelled inside a blood vessel by the indwelling device 1. Hereinafter, structures of the indwelling device 1 and the stent graft 10 according to the present embodiment will be described with reference to FIGS. 1 and 2. In the following description, for convenience, the right sides of sheets in FIGS. 1 and 2 are referred to as the base end sides, and the left sides of the sheets are referred to as the tip sides.

Figure 1A:
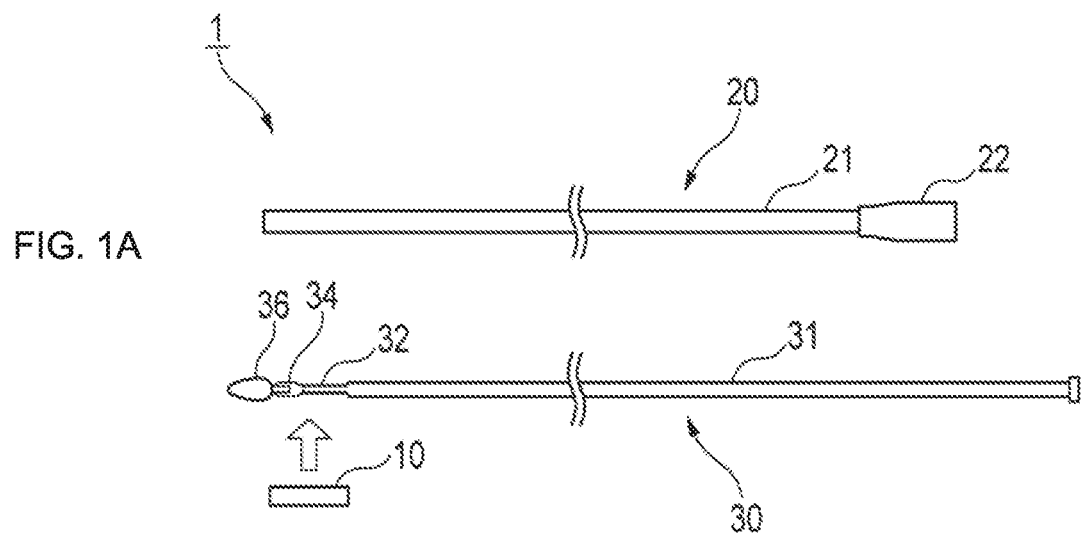
FIG. 1A shows each component composing an indwelling device for a cylindrical treatment tool according to an embodiment of the present invention.
Figure 1B:
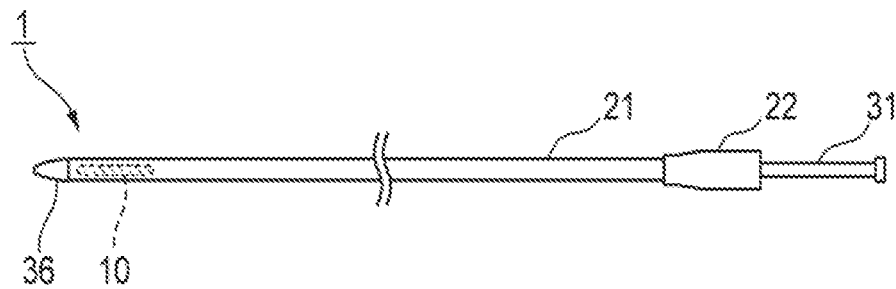
FIG. 1B shows the indwelling device assembled with each part.

As shown in FIGS. 1A and 1B, the indwelling device 1 includes a tubular sheath 20 and a tubular shaft 30, which is arranged inside the sheath 20 and configured to be capable of moving back and forth along the axial direction (longitudinal direction) of the sheath 20.

The sheath 20 has a sheath body part 21, and a hub 22 disposed at the end of the base end side of the sheath body part 21. The hub 22 has a nut (illustration omitted) or the like that fixes the shaft 30 to the sheath 20 or releases the fixing.

The sheath body part 21 is formed of a flexible material. Examples of the flexible material include biocompatible synthetic resin (elastomer) selected from fluorine resin, polyamide resin, polyethylene resin, polyvinyl chloride resin, and the like; a resin compound in which such resins are mixed with other materials; a multilayer structure made of such synthetic resins; and a composite of such synthetic resins and metal wire.

Figure 1C:
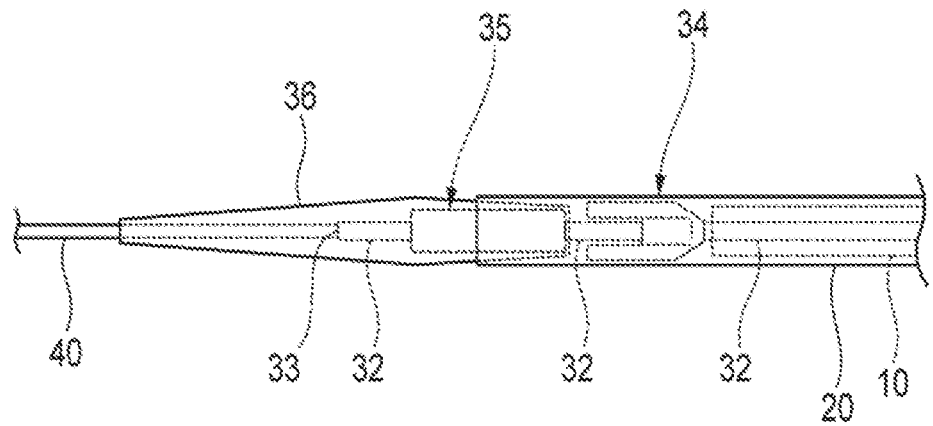
FIG. 1C is an enlarged view showing the internal structure of the tip of the indwelling device as perspective.

The shaft 30 is a shaft member including a tubular shaft body part 31 and a tubular smaller-diameter shaft part 32, which is coaxially continuous with the tip side of the shaft body part 31 as well as has a diameter smaller than that of the shaft body part 31. Inside the shaft 30, a hollow part 33 is continuously formed over the entire area in the axial direction (longitudinal direction). As shown in FIG. 1C, a metal guide wire 40 is inserted through the hollow part 33. Examples of the materials composing the shaft body part 31 and the smaller-diameter shaft part 32 include various materials having appropriate hardness and flexibility such as resins (plastic, elastomer, and the like) and metals.

The smaller-diameter shaft part 32 has a function of holding the stent graft 10 being contracted. Specifically, as shown in FIG. 1C, a fixture 34 is coaxially fixed to the smaller-diameter shaft part 32, and a hollow tube 35 is coaxially fixed at a position on the tip side apart from the fixture 34 with a gap. The fixture 34 and the hollow tube 35 are made to engage respectively with two types of engaging parts disposed on the stent graft 10 so as to control the radially outward movement of an opening of the stent graft 10 in a contracted state. Details of these two types of engaging parts, a connecting portion 14 and a blood vessel wall fixing portion 15, will be described later with reference to FIG. 2B.

On the hollow tube 35 and the end of the tip side of the smaller-diameter shaft part 32 projected from the hollow tube 35 to the tip side, the head chip 36 is disposed, which covers the outer circumferences of these as well as elongates taperedly further toward the tip side. The guide wire 40 is exposed from the tip opening of the head chip 36.

Examples of the materials composing the fixture 34 and the hollow tube 35 include various materials that have appropriate hardness and flexibility, such as resins (plastic, elastomer, and the like) and metals. Examples of the materials composing the head chip 36 include various materials with appropriate hardness and flexibility, such as synthetic resin (elastomer) composed of polyamide resin, polyurethane resin, polyvinyl chloride resin, and the like.

The smaller-diameter shaft part 32 has, for example, a diameter smaller than that of the shaft body part 31 by at least the thickness of the stent graft 10. In other words, when the shaft 30 is inserted inside the sheath 20, a space for holding the stent graft 10 is defined between the outer surface of the smaller-diameter shaft part 32 and the inner surface of the sheath body part 21. In this space, the stent graft 10 in a contracted state is held as described later. Here, the maximum diameter of the head chip 36 is, for example, substantially equal to the outer diameter of the sheath body part 21.

As shown in FIGS. 1B and 1C, the sheath 20 covers the stent graft 10 in a contracted state, as well as the fixture 34 and the hollow tube 35, and is capable of sliding relative to the shaft 30 up to a position to come into contact with the end of the base end side of the head chip 36. In this way, the stent graft 10 in a contracted state is made to be held in a contracted state by being covered with the sheath 20.

Figure 2A:
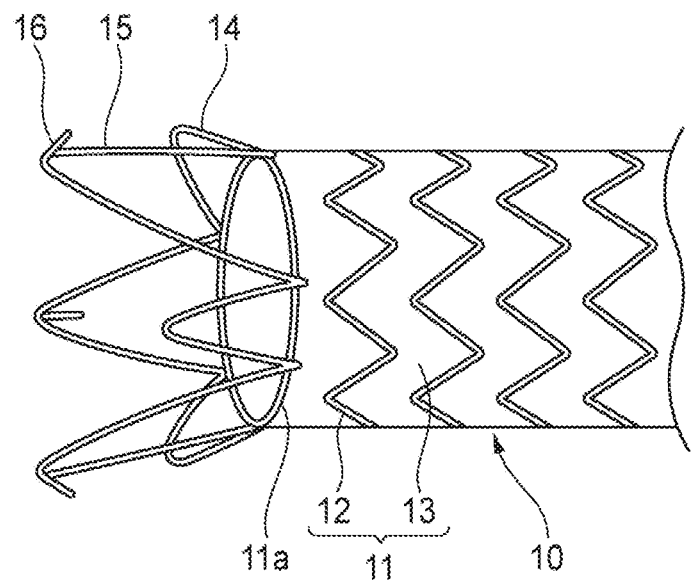
FIG. 2A is a perspective view showing the vicinity of one open end of a main part of the cylindrical treatment tool used in the indwelling device.

More specifically, as shown in FIG. 2A, the stent graft 10 has a main part 11 having a tubular shape that defines a flow path through which blood flow can pass. The main part 11 is configured with a skeleton part 12 and a film part 13. The stent graft 10 may have a straight tubular shape or, as appropriate, a curved tubular shape (e.g., as a shape compatible with the shape of a blood vessel of a patient). Moreover, the main part 11 may have a curved shape being preliminarily assumed for an indwelling site before indwelling, or may be made to have a curved shape along a blood vessel shape after indwelling.

The skeleton part 12 is configured to, for example, have a self-expanding wire mesh texture with a thin metal wire folded up and down in zigzags as well as formed into a tubular shape, and can be deformed from a contracted state, with contracting itself radially inward, to an expanded state, with expanding itself radially outward to define the cylindrical flow path. Examples of the materials composing the skeleton part 12 include known metals or metal alloys represented by stainless steel, Ni—Ti alloy, titanium alloy, and the like.

The film part 13 is fixed to the skeleton part 12 so as to cover the skeleton part 12 along the skeleton part 12 and defines the above-mentioned cylindrical flow path. Examples of the materials for the film part 13 include fluorine resin such as PTFE (polytetrafluoroethylene) and polyester resin such as polyethylene terephthalate.

One open end 11a of the main part 11 includes a connecting portion 14, which protrudes in a direction away from the open end 11a in the axial direction of the main part 11, and a blood vessel wall fixing portion 15, which protrudes in a direction away from the open end 11a in the axial direction and by a protrusion length longer than that of the connecting portion 14. At the protruding end part of the blood vessel wall fixing portion 15, for example, a fixing pin 16 for fixing the blood vessel wall fixing portion 15 to a blood vessel wall is disposed so as to protrude radially outward.

In the example shown in FIG. 2A, three of the connecting portions 14 and three of the blood vessel wall fixing portions 15 are disposed such that the connecting portions 14 and the blood vessel wall fixing portions 15 are alternately one-by-one positioned in the circumferential direction of the open end 11a. Each of the connecting portions 14 and each of the blood vessel wall fixing portion 15 are configured to have a self-expanding shape using a single thin metal wire that is folded up and down so as to protrude axially in a V shape from the open end 11a, and are capable of deforming from a contracted state, with contracting itself radially inward, to an expanded state, with expanding itself radially outward and contacting with the inner wall of a blood vessel (a blood vessel wall).

Here, the open end 11a preferably includes two or more of the connecting portions 14 and two or more of the blood vessel wall fixing portions 15, but the numbers of the connecting portions 14 and the blood vessel wall fixing portions 15 are an example and is not limited thereto, and can be arbitrarily changed as appropriate.

Figure 2B:
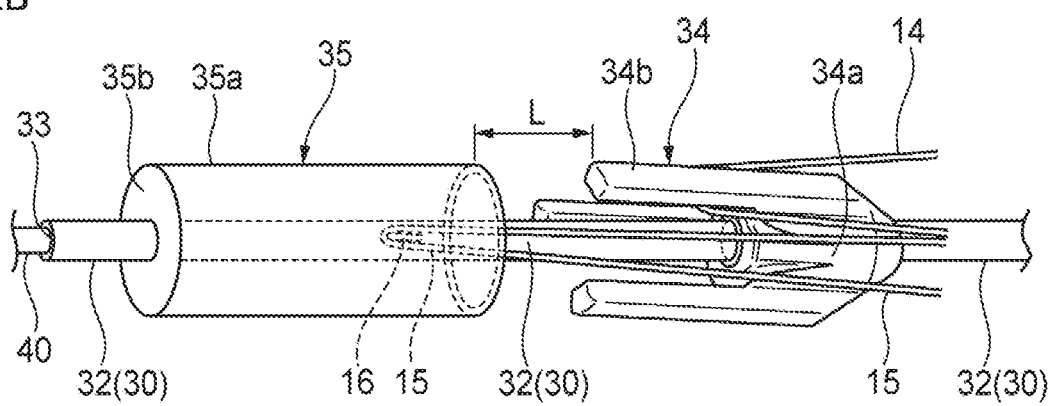
FIG. 2B is a view for illustrating a structure for maintaining the one open end of the main part of the cylindrical treatment tool in a contracted state.

As shown in FIG. 2B, the fixture 34 is configured with a fixture base part 34a, which is fixed to the smaller-diameter shaft part 32, and three columnar parts 34b, which extend linearly along the axial direction from the fixture base part 34a to the tip side. Here, FIG. 2B depicts one each of the connecting portions 14 and the blood vessel wall fixing portions 15, and omits depiction of others of the connecting portions 14 and the blood vessel wall fixing portion 15.

Each of the columnar parts 34b has, for example, a substantially rectangular parallelepiped shape that is slightly curved along the circumferential direction, and the surface on the axial center side of the smaller-diameter shaft part 32 is formed into a substantially flat surface. In addition, each of the plurality of the connecting portions 14 of the stent graft 10 is hooked on the corresponding columnar part 34b of the fixture 34 from the outside, thereby being held in a contracted state while being biased radially outward with self-expanding force. Moreover, the width along the circumferential direction of the tip of the columnar part 34b (a direction orthogonal to the axial direction and the radial direction) is smaller than, for example, the interval between the two ends on the base end side of the connecting portion 14, which forms the "V" shape in a contracted state, more specifically, the interval between the middle parts of the two arms opening to the base end side of the connecting portion 14.

The hollow tube 35 is arranged so as to be separated from the fixture 34 by a predetermined interval L.

The hollow tube 35 is configured to have a bottomed cylinder shape having a cylindrical part 35a and an end wall part 35b, which closes the opening on the tip side of the cylindrical part 35a. Furthermore, the smaller-diameter shaft part 32, which is inserted into the cylindrical part 35a having the opening on the base end side, is coaxially fixed to the end wall part 35b. The plurality of the blood vessel wall fixing portions 15 of the stent graft 10 has their protruding ends inserted into the hollow part of the hollow tube 35 by a predetermined length, thereby being held in a contracted state while being biased radially outward with self-expanding force.

Here, the depth from the base end side opening of the hollow part of the cylindrical part 35a to the tip-side bottom surface is, for example, larger than the length derived by summing the length of a part receiving insertion of the blood vessel wall fixing portion 15 and the axial length of the columnar part 34b. That is, as described later, the depth of the hollow part is set to an extent such that the tip of the blood vessel wall fixing portion 15 would not come into contact with the tip-side bottom surface of the hollow part of the cylindrical part 35a, even if the shaft 30 is moved to the base end side in order to release the catch of the connecting portion 14 on the columnar part 34b (see FIG. 4C).

Accordingly, the shaft 30 is displaced relative to the stent graft 10 from the state as shown in FIG. 2B, in which the fixture 34 and the hollow tube 35 are not covered by the sheath 20, toward the base end side, thereby also causing the fixture 34 to become displaced in the same direction so as to move the axial-center-side surface of columnar part 34b toward the connecting portion 14 side. Then, once the amount of displacement of the shaft 30 toward the base end side relative to the stent graft 10 is over the protruding length of the fixture 34 (the length of the columnar part 34b), the catch of the connection portion 14 on the columnar part 34b (a first engagement) is released. Just then, the plurality of the connection portions 14 is displaced radially outward with self-expanding force, passes through the gap corresponding to the predetermined interval L, and becomes in an expanded state, with expanding itself radially outward (see FIG. 4C).

In addition, when the shaft 30 is displaced toward the base end side relative to the stent graft 10 in this way, the blood vessel wall fixing portion 15 will be displaced inside the hollow part with maintaining a state of being inserted into the hollow part of the hollow tube 35. Specifically, at this time, the hollow tube 35 is relatively displaced toward the base end side relative to the blood vessel wall fixing portion 15. Thus, when the shaft 30 is displaced toward the base end side relative to the stent graft 10 in order to bring the connecting portion 14 into an expanded state, the blood vessel wall fixing portion 15 is securely maintained in a contracted state, without being accidentally brought into an expanded state, thus allowing the connecting portion 14 and the blood vessel wall fixing portion 15 to expand surely at different timings.

Furthermore, after the connecting portion 14 is in the expanded state, the shaft 30 is displaced toward the tip side relative to the stent graft 10, thereby also causing the hollow tube 35 to become displaced in the same direction. Then, once the amount of displacement of the shaft 30 toward the tip relative to the stent graft 10 is larger than the length of a part, in the blood vessel wall fixing portion 15, inserted into the hollow part of the hollow tube 35 in the state of FIG. 4C, the engagement between the protruding end of the blood vessel wall fixing portion 15 and the hollow tube 35 (a second engagement) is released. Just then, the blood vessel wall fixing portion 15 lets the protruding end move to the outside of the hollow part of the hollow tube 35 due to self-expanding force (move radially outward), passes through a gap corresponding to the predetermined interval L, and come into an expanded state, with expanding itself radially outward.

In this way, by moving the shaft 30, which has the fixture 34 and the hollow tube 35, toward the base end side and the tip side, each of the engagements of the connecting portion 14 and the blood vessel wall fixing portion 15 of the stent graft 10 with the fixture 34 and the hollow tube 35 can be released separately.

[Indwelling Procedure of the Cylindrical Treatment Tool]

Next, the procedure in indwelling the stent graft 10 on an affected area inside a blood vessel using the indwelling device 1 will be described with reference to FIGS. 3A to 3F and 4A to 4D. In FIGS. 3A to 3F, an example is shown where the stent graft 10 is indwelled on an affected area having an aneurysm 51 formed in a curved blood vessel 50. Here, in the following description, for convenience, the right sides of the sheets in FIGS. 4A to 4D are referred to as the base end sides, and the left sides of the sheets are referred to as the tip sides, as described above.

Figure 4A:
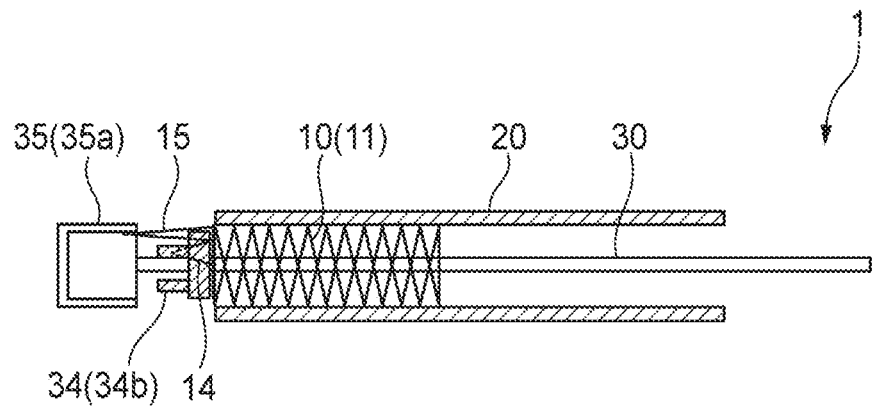
FIGS. 4A to 4D are schematic views showing transition of states of the indwelling device and the cylindrical treatment tool when the cylindrical treatment tool is indwelled into a blood vessel using the indwelling device.
Figure 4B:
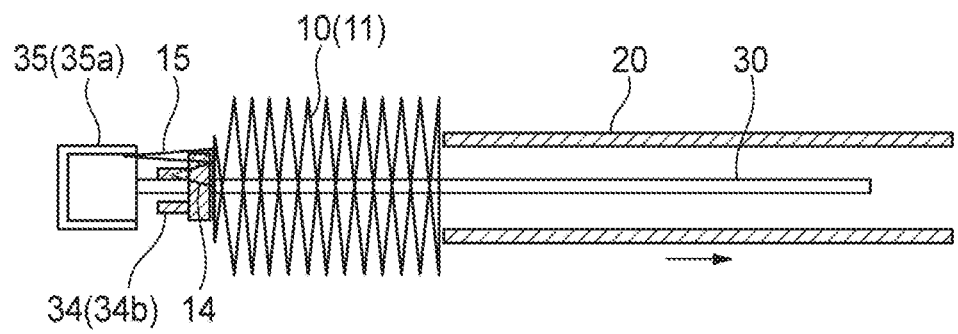

First, a guide wire 40, which is arranged inside the blood vessel 50 so as to pass through the affected area, is inserted through the shaft 30 from the tip side end of the indwelling device 1. In this state, the stent graft 10 is maintained in a contracted state by being covered with the sheath 20 (see FIG. 4A); inside the sheath 20, the connecting portion 14 of the stent graft 10 is hooked on the columnar part 34b of the fixture 34, to cause a state in which the blood vessel wall fixing portion 15 is inserted into the hollow tube 35. Note that FIG. 4A schematically shows a state in which the tip side part before the fixture 34 is exposed from the sheath 20.

Then, as shown in FIGS. 3A to 3C, the indwelling device 1 is advanced along the guide wire 40, which is inserted through the blood vessel 50 as described above.

Then, as shown in FIGS. 3D to 3E, with the position of the shaft 30 remaining fixed, the sheath 20 is moved so as to be pulled out, to release the stent graft 10 from inside the sheath 20. At this time, the main part 11 of the stent graft 10 is released outside from the sheath 20, thereby self-expanding radially outward (see FIG. 4B). As a result, the main part 11 of the stent graft 10 comes into close contact with the inner wall surface of the blood vessel 50 and is fixed to the inner wall surface. Note that at this point, the fixture 34 and the head chip 36 (specifically, the hollow tube 35) control the radial movement of the open end 11a of the stent graft 10, as described above.

Figure 4C:
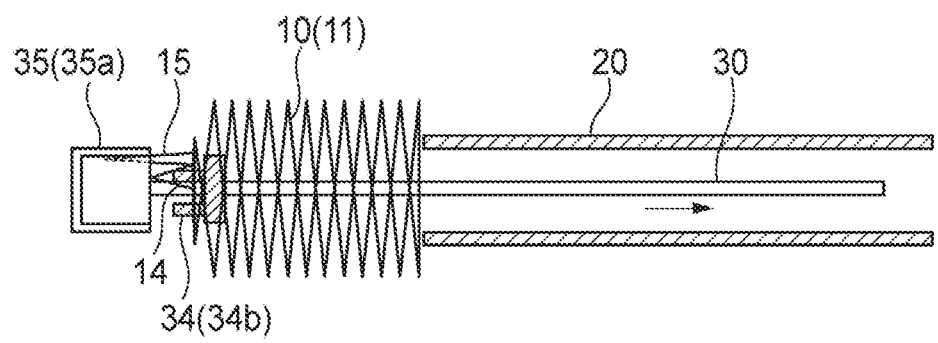

Then, the shaft 30 is displaced toward the base end side by a predetermined distance relative to the stent graft 10, which is fixed to the inner wall surface of the blood vessel 50 (see FIG. 4C). This releases the catch of the connecting portion 14 on the columnar part 34b, thereby bringing the plurality of the connecting portions 14 into an expanded state with self-expanding force. After that, the shaft 30 is further displaced toward the tip side relative to the stent graft 10 by a predetermined distance (see FIG. 4D). This moves the protruding end of the blood vessel wall fixing portion 15 to the outside of the hollow part of the hollow tube 35, thereby bringing the plurality of the blood vessel wall fixing portions 15 into an expanded state with self-expanding force.

As a result, as shown in FIG. 3F, the protruding ends of the plurality of the connecting portions 14 come into contact with the inner wall of the blood vessel 50, so that the plurality of the fixing pins 16, which is disposed at the protruding ends of the plurality of blood vessel wall fixing portions 15, comes into contact with the inner wall of the blood vessel 50, thereby firmly fixing the plurality of the blood vessel wall fixing portions 15 to the inner wall of the blood vessel 50.

After that, as shown in FIG. 3F, the guide wire 40 is withdrawn together with the sheath 20, thereby withdrawing the whole of the indwelling device 1. This completes indwelling of the stent graft 10.

[Action and Effect]

As described above, with the indwelling device 1 for the stent graft 10 according to the embodiment of the present invention, the single shaft 30, which has the fixture 34 and the hollow tube 35, can release separately each control of radial outward movements of the connecting portion 14 and the blood vessel wall fixing portion 15, and can provide the sheath 20 with a smaller outer diameter compared to one that multiply includes a plurality of shaft members, thereby enabling to reduce invasiveness to a patient's body. For example, it will be possible to provide easier passage through the blood vessel 50, such as the aorta and iliac artery, and also to reduce frequency of complications such as blood vessel damage. Furthermore, this allows the catheter to be directly (percutaneously) inserted into the blood vessel 50 to deliver or indwell the stent graft 10, thus enabling to reduce invasiveness to the patient's body more preferably.

In addition, since use of a single shaft 30 allows a space between the shaft 30 and the sheath 20 to be relatively wide, the sheath 20 having a relatively large outer diameter can be eliminated in housing of the stent graft 10, even in the case of, for example, the stent graft 10 having a relatively large outer diameter even in a contracted state, such as the stent graft 10 having a relatively large outer diameter or expansion force in an expanded state. That is, use of a single shaft 30 enables to employ the sheath 20 having a diameter smaller than that of the conventional ones, while enabling also to house the stent graft 10 having a relatively large outer diameter in a contracted state, even with use of the sheath 20 having an outer diameter similar to that of the conventional ones.

[Other Aspects]

It should be noted that the present invention is not limited to each of the embodiments described above, and can employ various modified examples within the scope of the present invention. For example, the material, shape, size, number, arrangement site, and the like of each element in the embodiments mentioned above are arbitrary and not limited as long as the present invention can be achieved.

In addition, the above-described embodiment has been illustrated with an alternate arrangement of the connecting portions 14 and the blood vessel wall fixing portions 15 in the circumferential direction at the open end 11a of the stent graft 10. However, this embodiment is an example, to which the present invention is not limited, and the arrangement of the connecting portion 14 and the blood vessel wall fixing portion 15 can be arbitrarily changed as appropriate. In other words, when relatively high fixing strength to the blood vessel wall is intended, it is preferable to dispose a relatively large amount of the blood vessel wall fixing portion 15 compared to the connecting portion 14. In contrast, when there is no need to increase fixing strength to the blood vessel wall from the blood vessel wall fixing portion 15, such as in the case where expanding force of the stent graft 10 is enough to allow fixation to the blood vessel wall, there may be no longer any need to dispose a number of the blood vessel wall fixing portion 15.

Moreover, the above-described embodiment has been illustrated with a portion having the fixing pin 16 as the blood vessel wall fixing portion 15. However, this embodiment is an example, to which the present invention in not limited, and it can be arbitrarily changed as appropriate whether the fixing pin 16 is equipped. In other words, when there is no need to increase fixing strength to the blood vessel wall from the blood vessel wall fixing portion 15, such as in the case where expanding force of the stent graft 10 is enough to allow fixation to the blood vessel wall, there is not always need to dispose the fixing pin 16 on the blood vessel wall fixing portion 15.

Figure 4D:
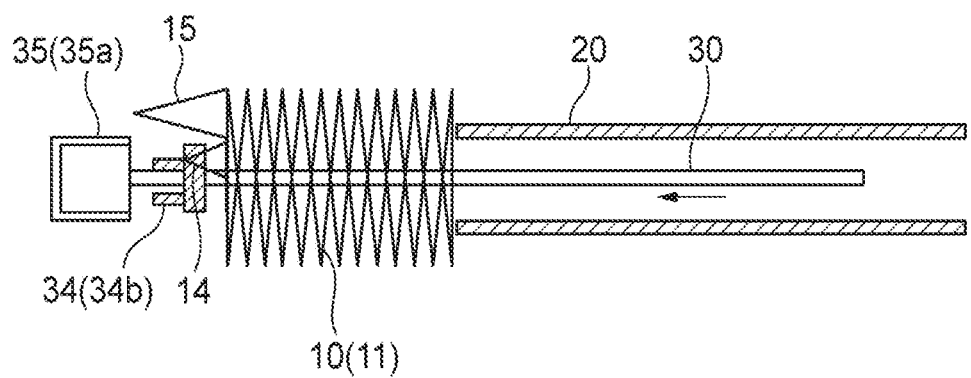

Additionally, in the above-described embodiment, as shown in FIGS. 4C and 4D, the shaft 30 is displaced toward the base end side relative to the stent graft 10, thereby releasing the engagement between the connecting portion 14 and the fixture 34, and subsequently, the shaft 30 is displaced toward the tip side relative to the stent graft 10, thereby releasing the engagement between the blood vessel wall fixing portion 15 and the hollow tube 35. Meanwhile, through appropriate adjustment of, for example, the axial length of the connecting portion 14 or the blood vessel wall fixing portion 15, the axial length of the fixture 34, the depth of the hollow tube 35, and the like, the shaft 30 may be displaced toward the tip side relative to the stent graft 10, thereby releasing the engagement between the blood vessel wall fixing portion 15 and the hollow tube 35, and subsequently, the shaft 30 may be displaced toward the base end side relative to the stent graft 10, thereby releasing the engagement between the connecting portion 14 and the fixture 34.

Furthermore, the above-described embodiment has been made as the shaft 30 is displaced toward the base end side relative to the stent graft 10, thereby releasing the engagement between the connecting portion 14 and the fixture 34, and is displaced toward the tip side, thereby releasing the engagement between the blood vessel wall fixing portion 15 and the hollow tube 35. However, this embodiment is an example, to which the invention is not limited. Any change can be arbitrarily made as appropriate, as long as a configuration is made in which the shaft 30 is axially displaced relative to the stent graft 10, thereby allowing the engagement between the connecting portion 14 and the fixture 34 and the engagement between the blood vessel wall fixing portion 15 and the hollow tube 35 to be released independently of each other. For example, a fixture is made that includes a plurality of columnar parts with different axial lengths in which the connecting portion 14 is engaged with the shorter columnar part and the blood vessel wall fixing portion 15 is engaged with the longer columnar part. Then, the shaft 30 may be displaced toward the base end side relative to the stent graft 10, thereby, first, releasing the engagement between the fixture and the connecting portion 14, and may be further displaced toward the base end side, thereby releasing the engagement between the fixture and the blood vessel wall fixing portion 15. In this case, there is no longer any need to equip the hollow tube 35, and the configuration of the indwelling device can be made simpler.

In addition, the above-described embodiment has been illustrated with the stent graft 10 to be indwelled and used inside the blood vessel 50. However, this is an example, to which the present invention is not limited, and for example, any tool may be used that is indwelled in a living body lumen other than a blood vessel (e.g., a gastrointestinal tract). Moreover, the cylindrical treatment tool according to the present invention may have a configuration in which the skeleton part 12 is not covered with the film part 13 (bare stent).

The content of disclosures in the specification, drawings, and abstract included in Japanese Patent Application No. 2018-051632 filed on Mar. 19, 2018 is incorporated into the present application in their entirety.

DESCRIPTION OF REFERENCE NUMERALS

1 Indwelling device
10 Stent graft (cylindrical treatment tool)
11 Main part
11a Open end
14 Connecting portion (first engaging part)
15 Blood vessel wall fixing portion (second engaging part)
16 Fixing pin
20 Sheath
30 Shaft (shaft member)
34 Fixture (first controlling part)
35 Hollow tube (second controlling part)
L Predetermined interval

The invention claimed is:

1. An indwelling device that causes a cylindrical treatment tool; which is radially expandable, to indwell a living body lumen, the indwelling device comprising:
a sheath in a tubular shape that is capable of housing the cylindrical treatment tool; and
an elongated shaft member sized and shaped to move back and forth inside the sheath along an axial direction of the sheath,
wherein the elongated shaft member has first and second controlling parts formed one after another along the axial direction;
wherein the first and the second controlling part engage with a first engaging part and a second engaging part provided at one end of the cylindrical treatment tool in the axial direction, respectively, to control radial movement of an opening end of the cylindrical treatment tool, and
wherein the elongated shaft member is displaced relative to the cylindrical treatment tool in one direction along the axial direction to allow release of a first engagement between the first controlling part and the first engaging part, and displaced relative to the cylindrical treatment tool in a direction other than the one direction along the axial direction to allow release of a second engagement between the second controlling part and the second engaging part to be released independently of each other.

2. The indwelling device according to claim 1,
wherein the second engaging part of the cylindrical treatment tool is disposed at a position different from a position of the first engaging part in the axial direction.

3. The indwelling device according to claim 2, wherein the second controlling part makes the second engagement with the second engaging part unreleasable even when the elongated shaft member is displaced relative to the cylindrical treatment tool in the one direction during the release of the first engagement.

4. The indwelling device according to claim 2, wherein the second controlling part has a hollow part capable of engaging with the second engaging part, which is inserted into the hollow part, and is displaceable in the one direction while maintaining a state of the second engaging part being inserted into the hollow part when the elongated shaft member is displaced relative to the cylindrical treatment tool in the one direction.

5. The indwelling device according to claim 2,
wherein the first engaging part protrudes in a direction away from the opening end in the axial direction by a predetermined protrusion length, and
wherein the second engaging part protrudes in the direction away from the opening end in the axial direction by a protrusion length longer than the predetermined protrusion length of the first engaging part.

6. The indwelling device according to claim 1,
wherein the first controlling part and the second controlling part are arranged on the elongated shaft member with a gap in the axial direction, and
wherein the gap defines a space allowing release of the first engagement and radial movement of the first engaging part upon displacement of the elongated shaft member in the one direction, and defines a space allowing release of the second engagement and radial movement of the second engaging part upon displacement of the elongated shaft member in the direction other than the one direction.

7. The indwelling device according to claim 1, wherein the second engaging part has a fixing pin to fix the cylindrical treatment tool to an inner wall of the living body lumen.

8. A cylindrical treatment tool that is caused to indwell a living body lumen using an indwelling device including an elongated shaft member, the cylindrical treatment tool comprising:
- a main part in a tubular shape configured to radially expand; and
- a first engaging part and a second engaging part each protruding in a same direction away from one opening end of the main part in an axial direction of the main part by a predetermined protrusion length and configured to engage with the elongated shaft member,
- wherein the first engaging part and the second engaging part each engage with the elongated shaft member to allow control of radial movement of the one opening end,
- the first engaging part is configured to allow release of a first engagement with the elongated shaft member by relative displacement of the cylindrical treatment tool and the elongated shaft member in one direction along the axial direction, and
- the second engaging part is configured to allow release of a second engagement with the elongated shaft member by relative displacement of the cylindrical treatment tool and the elongated shaft member in a direction other than the one direction along the axial direction.

* * * * *